(12) United States Patent
Kim

(10) Patent No.: US 8,323,213 B2
(45) Date of Patent: Dec. 4, 2012

(54) QUANTITATIVE AND QUALITATIVE ANALYSIS APPARATUS FOR MEASURING THE BODY FLUID

(75) Inventor: Kyoung-Hun Kim, Seoul (KR)

(73) Assignees: Hanmedics Co., Ltd., Seoul (KR); Kyoung-Hun Kim, Seoul (KR)

( * ) Notice: Subject to any disclaimer, the term of this patent is extended or adjusted under 35 U.S.C. 154(b) by 863 days.

(21) Appl. No.: 12/084,978

(22) PCT Filed: Nov. 15, 2006

(86) PCT No.: PCT/KR2006/004797
§ 371 (c)(1),
(2), (4) Date: May 14, 2008

(87) PCT Pub. No.: WO2007/058461
PCT Pub. Date: May 24, 2007

(65) Prior Publication Data
US 2010/0228148 A1 Sep. 9, 2010

(30) Foreign Application Priority Data

Nov. 15, 2005 (KR) .................. 10-2005-0109136
Nov. 14, 2006 (KR) .................. 10-2006-0112504

(51) Int. Cl.
B65D 81/00 (2006.01)
A61M 27/00 (2006.01)
A61M 1/00 (2006.01)
A61F 5/44 (2006.01)
A47K 3/022 (2006.01)
A47K 3/26 (2006.01)
A47K 11/00 (2006.01)
A61H 35/00 (2006.01)

(52) U.S. Cl. ........ 600/584; 600/574; 604/544; 604/318; 604/327; 604/346; 4/443; 4/144.1

(58) Field of Classification Search .................. 600/573, 600/574, 584, 580–582; 604/317–357, 544; 4/443–448, 144.1–144.3
See application file for complete search history.

(56) References Cited

U.S. PATENT DOCUMENTS

| 1,809,714 | A | * | 6/1931 | Mathews | 219/522 |
| 4,343,316 | A | * | 8/1982 | Jespersen | 600/584 |
| 4,631,061 | A | * | 12/1986 | Martin | 604/318 |
| 4,712,567 | A | * | 12/1987 | Gille et al. | 600/584 |
| 5,551,097 | A | * | 9/1996 | Short | 4/301 |
| 5,882,931 | A | | 3/1999 | Petersen | |

(Continued)

FOREIGN PATENT DOCUMENTS

| KR | 10-0395342 B1 | 8/2003 |
| KR | 10-0494365 B1 | 6/2005 |

*Primary Examiner* — Max Hindenburg
*Assistant Examiner* — John Pani
(74) *Attorney, Agent, or Firm* — Birch, Stewart, Kolasch & Birch, LLP

(57) ABSTRACT

A quantitative and qualitative analysis apparatus of a body fluid serves as a replacement of a Foley catheter and a urine bag connected The analysis apparatus is capable of automatically measuring the volume of a body fluid (urine volume) and specific constituents in a body fluid (urine and blood) in a real time mode and is capable of outputting the measurement results with ease, thereby promoting the efficiency of human resource management so that medical staff may be able to make a quick diagnosis on the current state of the patient based on the provided data and thus, take all necessary measured to improve the patient's condition at proper time.

8 Claims, 16 Drawing Sheets

U.S. PATENT DOCUMENTS

| | | |
|---|---|---|
| 6,665,889 B2 * | 12/2003 | Kim .................................. 4/443 |
| 6,698,583 B2 | 3/2004 | Itoh |
| 2003/0017464 A1 * | 1/2003 | Pohl ................................ 435/6 |
| 2003/0181826 A1 * | 9/2003 | Smith et al. .................... 600/581 |
| 2005/0288571 A1 * | 12/2005 | Perkins et al. ................. 600/407 |
| 2007/0010797 A1 * | 1/2007 | Nishtala et al. ............... 604/540 |

* cited by examiner

QUANTITATIVE AND QUALITATIVE ANALYSIS APPARATUS FOR MEASURING THE BODY FLUID

FIELD OF THE INVENTION

The present invention relates to a quantitative and qualitative analysis apparatus of a body fluid, and more particularly to an analysis apparatus capable of measuring volume of body fluid excretion of patients, especially urine volume, and analyzing specific constituents of body fluids such as urine and blood, which include urea, sodium cation ($Na^+$), pH, glucose, BUN, creatine (Cr), and protein.

BACKGROUND OF THE INVENTION

Body fluids include all types of liquid phase substances contained in a body of an animal or a human. Although body fluids in general refer to whole blood, lymph, urine, saliva, sweat and the like, the present invention is particularly related to blood and urine of a human body (a patient for example).

Measurement of urine volume of a patient is an important factor for the evaluation of circulating blood volume.

A human body goes into a circulatory collapse state due to the direct reduction of circulatory blood volume such as blood loss, burns and so on caused by all kinds of accidents or surgeries, and due to the indirect reduction of circulatory blood volume such as sepsis (blood infection) and heart failure (myocardial infarction, arrhythmia, etc.). When such occurs, small arteries contracts regardless of whether the autonomic (sympathetic and parasympathetic) nervous system is under conscious control, and this affects blood volume to be supplied to every organ in the body.

Among the organs, a kidney suffers the most serious arterial contraction. This is because it is the kidney that filters blood flowing therein to thereby form urine, thereby contributing to the reduction of a circulating blood volume.

Under the neural regulation of the autonomic nervous system, contraction of kidney arteries plays a role in blocking the volume of blood flow into the kidney in the early stage of hematozemia and a role in suppressing urine production, so that the circulating blood volume can be preserved. However, if this state is continued over the span of hours (6 hours or longer), renal cells get severely damaged and acute tubular necrosis (ATN), a kidney disorder associated with the development of acute renal failure, may occur or permanent kidney failure may be resulted in, depending on the conditions of a patient.

In field or clinical experiences, if a patient loses much blood because of internal diseases or during accidents/surgeries, he is provided with fluid (Ringer's solution: physiological saline) to prevent the above-described side effects and further to normalize the circulating blood volume. This consequently induces the relaxation in the small arteries supplied to the kidney, and prevents necrosis in renal tubule cells.

One of the most crucial criteria that shows whether a proper circulating blood volume is restored after the physiological saline was replenished, and whether an adequate volume of blood flow is provided into the kidney, is measuring the urine volume. In effect, urine volume is the very first thing medical staffs check in a patient after loss of the circulating blood volume was replenished through the fluid (Ringer's solution).

Monitoring an intake with an output of the body, one can evaluate whether or not the kidney is properly functioning and whether a proper volume of the blood is being circulated.

Some of specific constituents contained in blood and urine are used as very important criteria for the evaluation of renal function.

Information in Table 1 below is used in a real clinical experience to check a patient's condition.

TABLE 1

GFR (glomerular filtration ratio): Criteria: Creatinine clearance (Ccr)
(Normal range of GFR: 150 L/day or 100 mL/min)
Ccr (ml/min) = (Urine Cr × Volume/Plasma Cr)
Urine Cr: mg/dl, Volume: mL/min, Plasma Cr: mg/dL As can be seen in Table 1, urine volume, and creatine (Cr) in urine or in blood shows a value of Cr clearance, and its value reflects GFT (glomerular filtration ratio), namely, the clearing capability or filtering ability of the kidney, useful for the renal function test.

TABLE 2

| Formula | Pre-renal ARF (n value) | Intrinsic renal ARF (n value) |
|---|---|---|
| Cr ratio = Urine Cr/Plasma Cr | >40 | >20 |
| Plasma BUN/Cr ratio | >20 | |
| Nitrogen ratio = Urine BUN/Plasma BUN | >8 | |
| Urine Osmolarity | >500 | |
| Specific gravity | >1,018 | |
| Concentration of $Na^+$ in Urine | | >20 |
| ★ FE $Na^+$ = Urine ($Na^+$/Cr)/Plasma ($Na^+$/Cr) | <1 | >1 |
| ★ Renal Failure Index = U ($Na^+$)/GFR = Urine $Na^+$/(urine Cr/Plasma Cr) | <1 | >1 |

As can be seen in Table 2, when constituents of blood and urine, i.e., Cr, BUN, and $Na^+$, Osmolarity, specific gravity and so on are known, one can estimate a cause of ARF. 'Pre-renal ARF' in Table 2 indicates that the cause already existed, meaning that the deficiency of blood volume itself results from diseases. 'Intrinsic renal ARF' indicates that the kidney itself has a problem, meaning that damages are brought on renal cells by various causes.

Among the criteria, FE $Na^+$ value and Renal Failure Index value marked with ★ are the most accurate, and therefore used as the most valuable criteria in field.

For instance, if the result of FE $Na^+$ obtained by substituting $Na^+$ and Cr concentrations in the equation is greater than 1, it indicates renal failure due to damaged renal cells of a patient. On the other hand, if the result is less than 1, it means that the patient's kidney functions normally but the circulating blood volume is deficient. In like manner, results of the Renal Failure Index can be utilized.

As such, measurement of urine volume and specific constituents in blood and in urine signifies much about patients suffering from direct, acute blood loss because of accidents, surgeries, burns and so on, or patients with internal diseases.

Besides the evaluation of acute renal diseases, the measurement can enable early diagnosis and prognosis of a chronic renal disease, that is, an accurate monitoring of the progress of a disease. Typical examples of such are heart failures like diabetic chronic renal disease.

On the other hand, most critically ill patients and ABR (absolute bed rest) patients are hospitalized due to various internal diseases. For medical management of such a patient group, a Foley catheter is currently used.

The Foley catheter passes through a urethra into a patient's bladder and is held therein through blooning. The urine stored in the bladder through the Foley catheter is collected in a urine bag by internal pressure, and the accumulated urine volume is measured through the scaled marked on the bag.

Basically, operating procedure requires the insertion of the Foley catheter from the entrance of the urethra down to the bladder, so a patient feels a lot of pain during the procedure. In addition, it may cause a secondary infection such as urinary system infection and contributes to the mass production of antibiotic resistant strains in a hospital. If the urinary system infection through the Foley catheter results in hematogenous infection, it may prove fatal. It has been reported that if the urinary system infection progresses to the hematogenous infection, the mortality rate reaches approximately 30% (refer to Internal Medicine Cecil).

In a hospital, if symptoms of infection, e.g., chill, fever etc., are actually observed after the Foley catheter insertion operation required for measurement of urine volume in a real time mode, the first step is to remove the Foley catheter, administer a suitable antibiotic, and carry out postprocessing depending on the course. Unfortunately if the patient has an underlying disease, he might permanently lose renal function.

The conventional technique for measurement of urine volume by reading scales marked on the urine bag connected to the Foley catheter has three major problems as follows:

First of all, it is not reliably accurate. The urine bag has different shapes depending on how it is fixed to the bedside and what state it is in, and those different shapes give different scales on an actual height of the urine volume accumulated in the bag. This type of scale reading has a great margin of observational error.

Secondly, it is neither convenient nor efficient. Although it may be different depending on the condition of a patient, if a doctor gives an order to measure the urine volume, a nurse or the patient's patron or caregiver should personally check urine in the urine bag every hour. If an emergency patient comes to the ward, all staff in the hospital pay attention to that patient, so other patients except for the emergency patient naturally lose interest of doctors.

Thirdly, it causes a secondary infection through the Foley catheter. This is actually the most serious problem, with about 30% of patients who have the Foley catheter operation reported to suffer from the urine system infection 1 week after the operation (refer to General Surgery Sabiston). This urinary system infection increases 3 to 5% every day. If it is neglected more than 2 weeks, almost every patient will suffer from the urinary system infection (refer to Internal Medicine Cecil).

As an attempt to solve the above-described problems, the inventors have suggested diverse urine collecting instruments for more conveniently collecting urine from patients with and without urination troubles like dysuria.

Korean Patent Application Nos. 2000-47602, 2000-58206, 2001-86938, and 2002-44362 filed by the same inventors disclosed a urine collecting apparatus that automatically senses urine, sucks and cleanses the urine with a bidet, even for use with an unconscious patent.

Even though these inventions improved the reading accuracy of the existing urine bag in that they measure the urine volume through the scales marked on a urine container, they still require an individual to personally read the scales for measurement. After all, the inventions show no improvement in the inconvenient conventional method, and do not consider constituents of the urine, either.

In addition, in case of the previously disclosed inventions, the urine collecting apparatus has the structure shown in FIG. 9, where a urine container 26 for keeping a urine case is installed on the rear end portion of the apparatus and a urine passage 27 is extended in a longitudinal direction and at the same time, the crooked passage is directed against gravity as shown in the drawing. Therefore, if the apparatus is used for an extended period of time, urinary calculus is easily formed in the passage, easily producing odor if the apparatus is not maintained in hygienic conditions.

Moreover, because the urine container and a scrubbing water container are installed in the same space, it is highly likely that the scrubbing water container becomes contaminated rather easily, in spite of strong demand for hygiene standards therefor.

Meanwhile, the existing analysis of constituents in a body fluid is generally made with help of an instrument in a clinical laboratory. For the analysis, a specific chemical is first added to the body fluid and a spectrum is used to analyze constituents therein. Normally, it takes more than 24 hours from the analysis to informing the analysis results to the medical staff concerned. The reason for delay is because technicians in the laboratory do not always handle one single urine sample of a particular individual but they test urines of all patients hospitalized in a hospital, label their body fluid samples, analyze batches of the samples, and match the analysis results with names of the respective patients.

SUMMARY OF THE INVENTION

Therefore, an object of the invention to provide a novel quantitative and qualitative analysis apparatus for measuring the body fluid, which detects urination time and urine volume each time to calculate total urine volume per day and further an average urine volume each time; senses a urination frequency and a main time period of urination to check conditions of urine (e.g., enuresis, frequent urination, encopresis and so on); immediately analyze (within 1 minute) specific constituents in urine and blood; and includes a controller that calculates ★ FE $Na^+$ value and Renal Failure Index value by Equations given in Table 2, to thereby diagnose the condition of a patient without delay and to help medical staff take all necessary measures for improving the patient's condition.

In this manner, the present invention is capable of preventing side effects, such as a secondary infection of urinary system, caused by the Foley catheter inserted into every patient's body regardless of whether the patient has urinary problems or not. By selectively inserting the Foley catheter into patients depending on whether the patients have urination troubles, patients without urination troubles may be protected from the urinary infection from the beginning.

Moreover, the apparatus of the invention is designed to be able to automatically measure and output urine volume so that it can be usefully applied to patients with urination troubles, and manpower of medical staff can be managed more efficiently by substantially improving the inefficient conventional measurement method of urine volume that required medical staff or caregiver to personally check and record urine volume collected in a urine bag on an hourly basis.

Another object of the present invention is to provide a novel quantitative and qualitative analysis apparatus for measuring the body fluid, which the apparatus features an improved hygiene structure compared with the previous urine collecting apparatus and bidet developed by the inventors, so that it may be used by many people without causing contamination problems. Further, a patient can easily operate the apparatus and measure his body fluid sample for himself within one minute from the urine collection.

The present invention has improved scale reading accuracy and efficiency of the conventional urine bag. In particular, in case of a patient with no urination trouble, constituents of his body fluid (urine, blood and the like) can be measured or analyzed in a real time mode without inserting the apparatus directly into the his body. The data is then provided immediately to the medical staff, thereby helping them take proper measures to improve the patient's condition. In addition, unlike the conventional Foley catheter, the present invention apparatus can contribute to a substantial reduction in the side effects such as urinary system infection, and provide more hygienic and efficient medical care facilities.

On the other hand, in case of a patient with urination troubles, the urine bag connected to the insertion type Foley catheter as depicted in FIG. 19 may be connected to the body of the present invention apparatus, or the main body of the present invention apparatus having a built-in load cell connected to the lower part of a urine collecting unit (FIG. 17b) or to the lower ring of the upper case of the main body may be used to measure the urine volume in mass.

In accordance with an aspect of the present invention, there is provided a body fluid collecting apparatus with a bidet system, which includes a body fluid collector for collecting the body fluid (urine) discharged from a patient; a body fluid container for storing the body fluid; a cleansing water container for storing cleansing water used in the body fluid collector; a driving unit for moving the body fluid (urine) from the body fluid collector into the container and for moving the cleansing water in the cleansing water container into the body fluid collector; a control unit for controlling the operation of the driving unit; a measuring unit for measuring quantity and constituents of the body fluid (urine) drained in the body fluid collector; and an output unit for outputting a measurement value obtained by the measuring unit, the measuring unit and the output unit being housed in a body of the apparatus.

The measuring unit has two parts: one for measuring volume of the body fluid (urine) and the other for measuring constituents in the body fluid (blood, urine and the like).

There are two technical schemes useful for quantitation of the body fluid (urine). One of them is the combination of a fluid sensing device (Korean Utility Model Registration No. 320686, herein incorporated by reference) and a fluid measuring device using an optical sensor (Korean Patent Application No. 2005-97584, herein incorporated by reference). This is the most preferred constitution for realizing the functions of the present invention. The other makes use of Doppler Effect.

Meanwhile, a technical scheme useful for measuring or analyzing constituents of the body fluid (blood, urine) incorporates a biosensor (Korean Patent Application No. 2005-516645, herein incorporated by reference) into the present invention apparatus. This is the most preferred constitution to carry out the present invention.

Particularly, the control unit of the present invention is involved in inputting and storing a measurement value provided from the measuring unit, and outputting the result through a specific output unit. In addition, the control unit substitutes the data obtained by the measuring unit to given equations (i.e., FE $Na^+$ and Renal Failure Index equations) to thereby diagnose clinical conditions of patients based on the operation results.

The output unit of the present invention outputs data values that had been obtained by the measuring unit and adjusted by the control unit through a means such as a display, a built-in printer, an enclosure printer, a USB port, an RF device, a bluetooth and the like. The output unit makes it possible to efficiently manage the medical field and to provide telemedicine services to patients in their homes.

Moreover, long term residential lease or rental can be available to help more people benefit from the present apparatus. As part of an improved hygiene structure, the inventors modified the illogical structure of prior urine collecting device to ensure that no remainder is deposited in the catheter, isolating a contaminant, and using a disposable pack, thereby enabling a hygienic and convenient management of the apparatus.

The other objectives and advantages of the invention will be shown and described with reference to certain preferred embodiments thereof, it will be understood by those skilled in the art that various changes in form and details may be made therein without departing from the spirit and scope of the invention.

DESCRIPTION OF THE DRAWINGS

The above and other objects, features and other advantages of the present invention will be more clearly understood from the following detailed description taken in conjunction with the accompanying drawings, in which:

FIG. 2 shows exploded perspective views of a quantitative and qualitative analysis apparatus according to other embodiments of the present invention, in which

DETAILED DISCLOSURE OF THE INVENTION

Hereinafter, preferred embodiments of the present invention will be set forth in detail with reference to the accompanying drawings.

Figure 1:
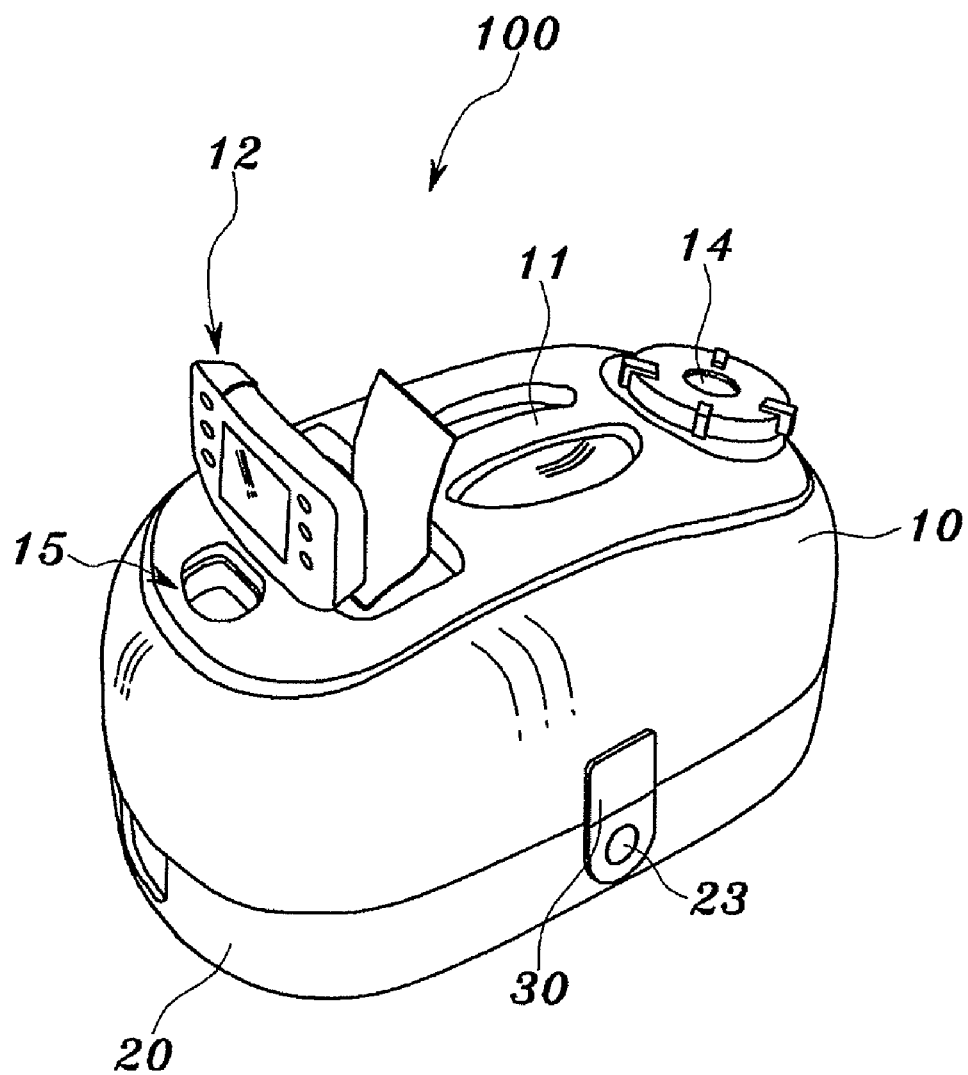
FIG. 1 is a perspective view of a quantitative and qualitative analysis apparatus of a body fluid according to a preferred embodiment of the present invention.

FIG. 1 is a perspective view of a quantitative and qualitative analysis apparatus of a body fluid according to a preferred embodiment of the present invention. An adapter (FIG. 5) on the tip of a body fluid collector (not shown, refer to Korean Patent No. 44362, herein incorporated by reference) is plugged into a joint socket 15 formed in a body 100 of the analysis apparatus of the invention, so that the analysis apparatus 100 can measure the volume and constituents of a body fluid as a body fluid supplied through the body fluid collector passes through it.

Figure 2A:
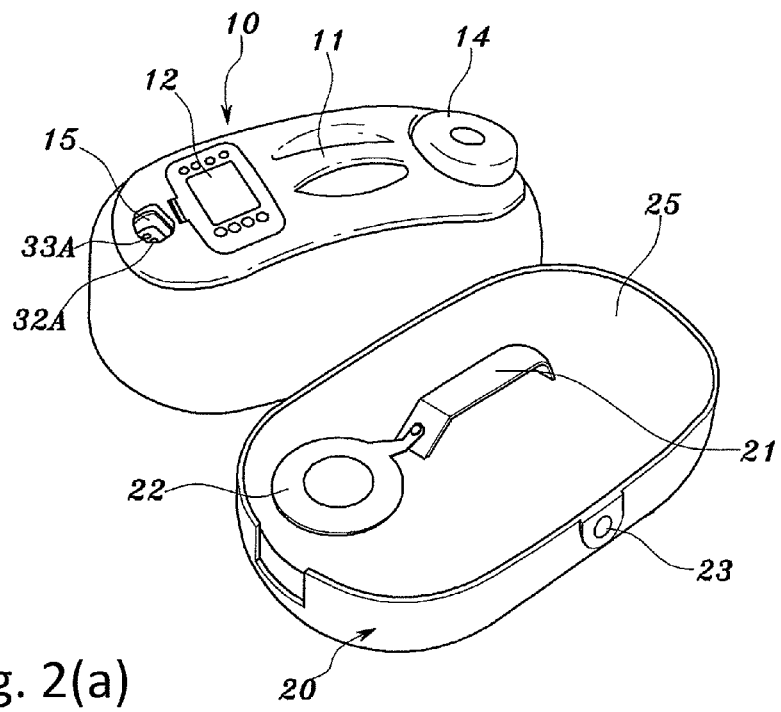
FIG. 2a is an exploded perspective view showing a disassembly of an upper case and a lower case built in a vertically detachable manner and FIG. 2b is an exploded perspective view showing a disassembly of an upper case and a lower case built in a manner that the lower case is slidable anteroposteriorly into and out of the upper case.
Figure 2B:
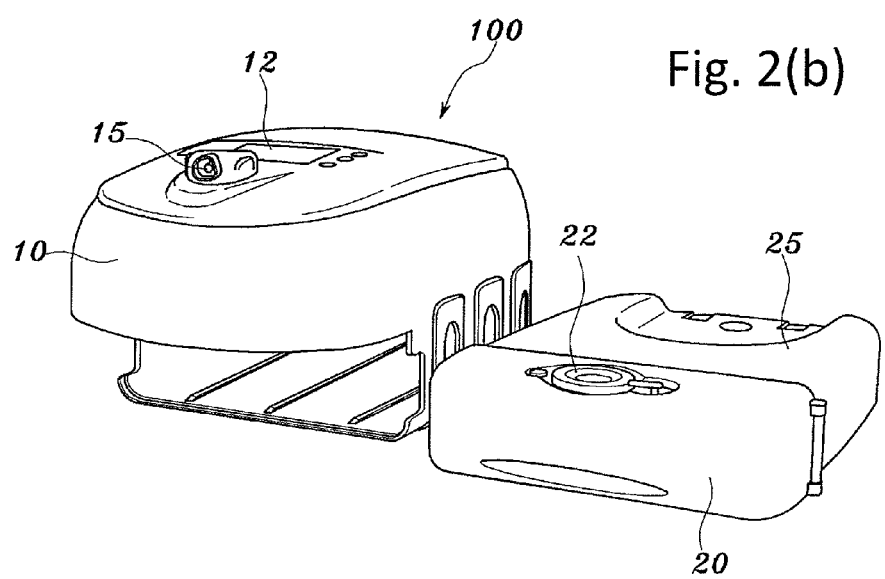

As depicted in FIGS. 2a and 2b, the body 100 includes an upper case 10 and a lower case 20. In particular, FIG. 2a illustrates that the upper case and the lower case are built in a vertically detachable manner, and FIG. 2b illustrates that the lower case is built in a manner slidable into and out of the upper case anteroposteriorly.

Figure 3:
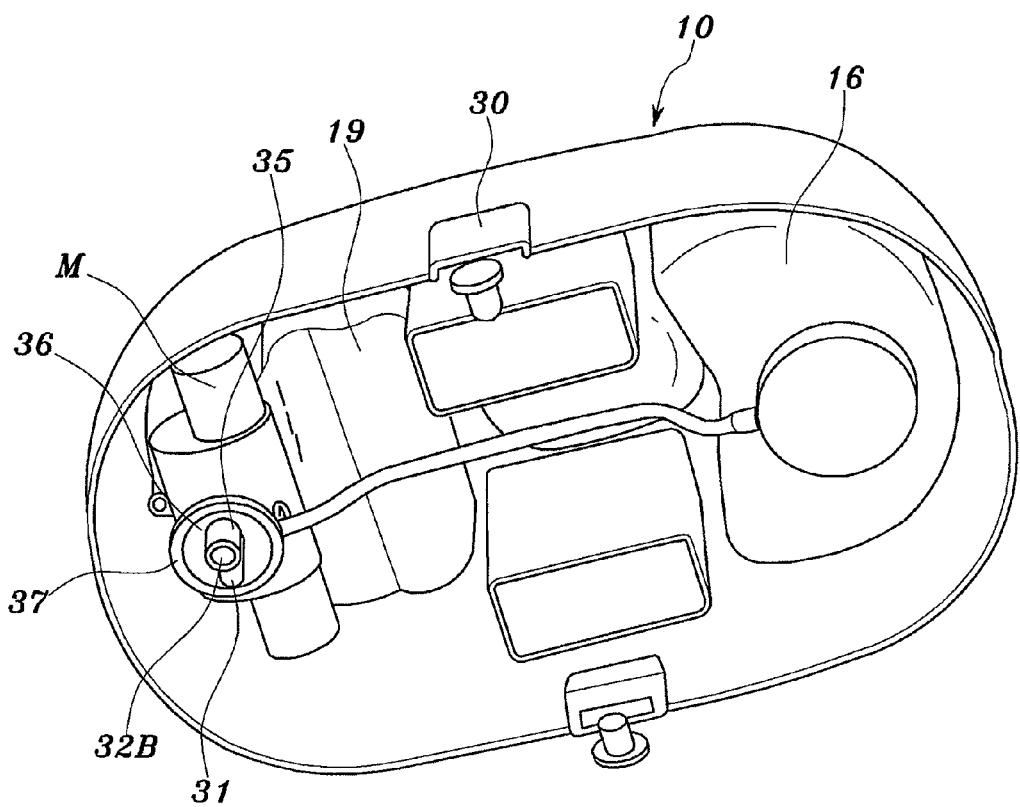
FIG. 3 shows a detailed rear perspective view of the upper case of the analysis apparatus according to the present invention.

Referring to FIG. 3, the upper case 10 and the lower case 20 are designed to be detachable/attachable from/to each other in a vertical direction by a button 30 with an elastically mounted spring on one side of the central part of the outer surface of the lateral wall.

Now that the upper case and the lower case of the analysis apparatus of the present invention are detachable from each other, the container that is relatively more susceptible to contamination may be isolated separately from the other constituents and be hygienically treated to ensure safe use (FIGS. 2a and 2b).

Figure 16:
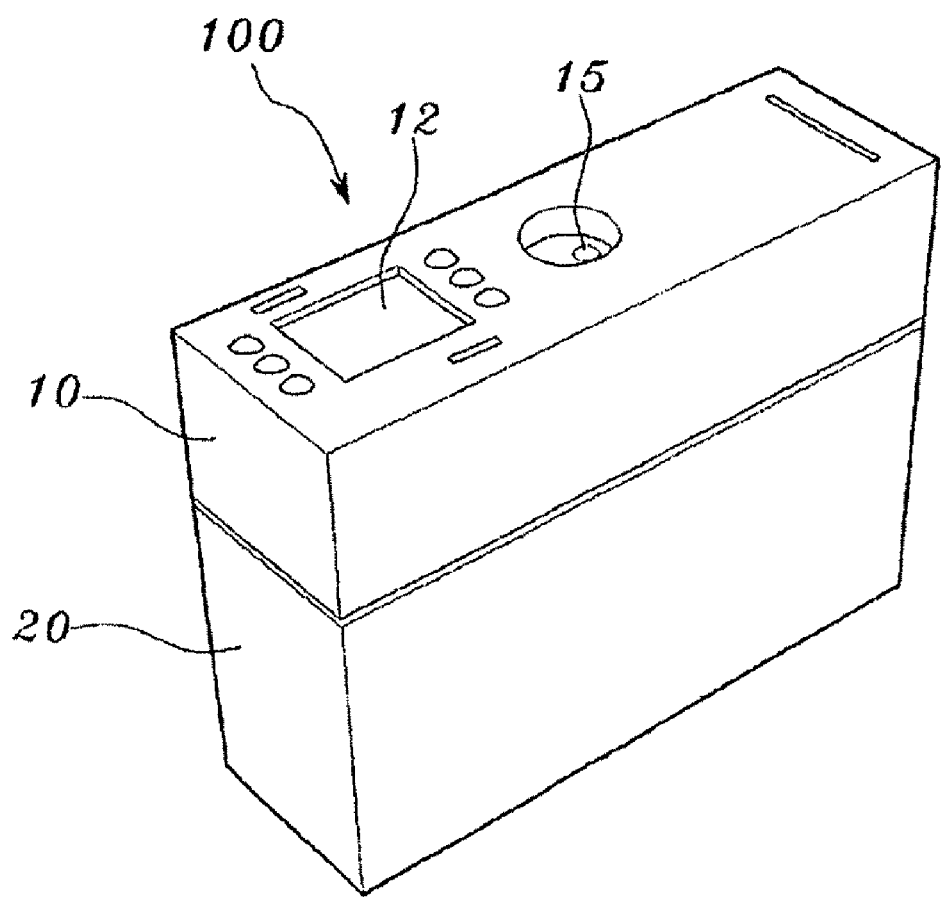
FIG. 16 is a perspective view of an analysis apparatus provided with a built-in load cell suitable for use with a patient having an urination trouble (or dysuria) according to still another embodiment of the present invention.
Figure 17:
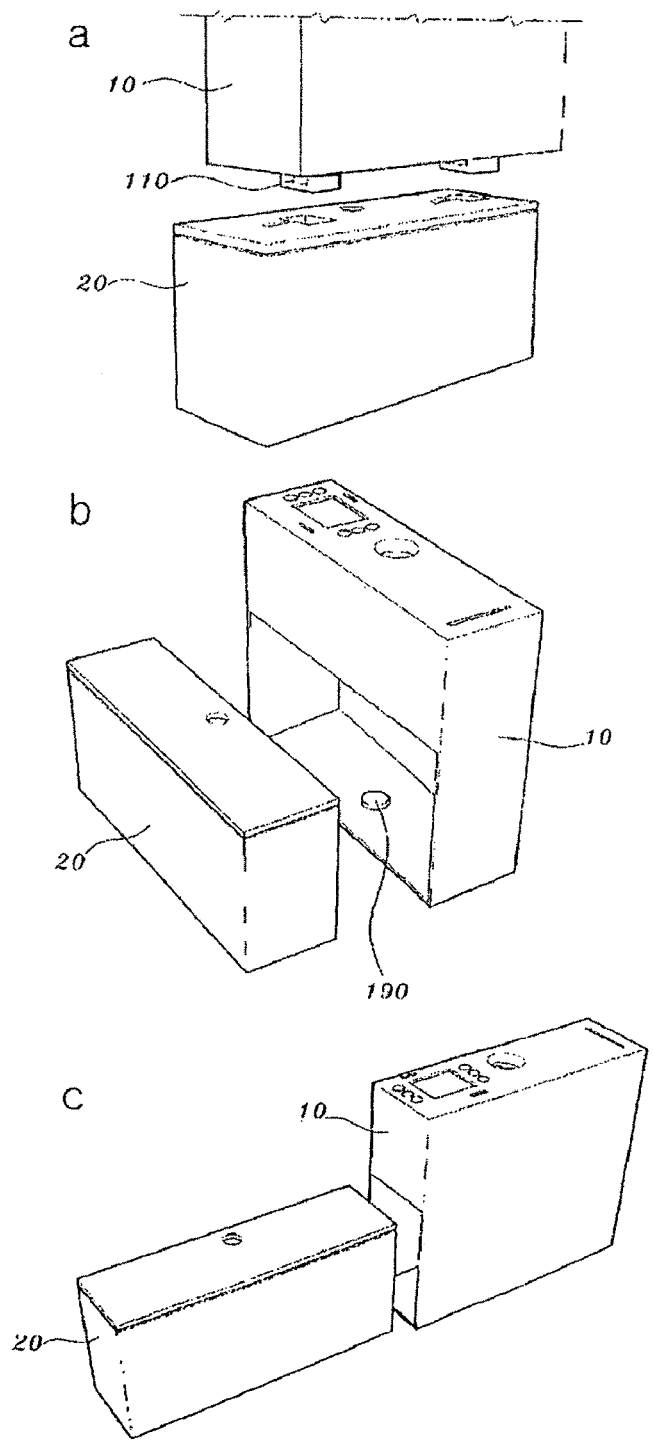
FIG. 17 shows perspective views of diverse patterns of the assembly of the analysis apparatus appropriate for a patient having an urination trouble.
Figure 18:
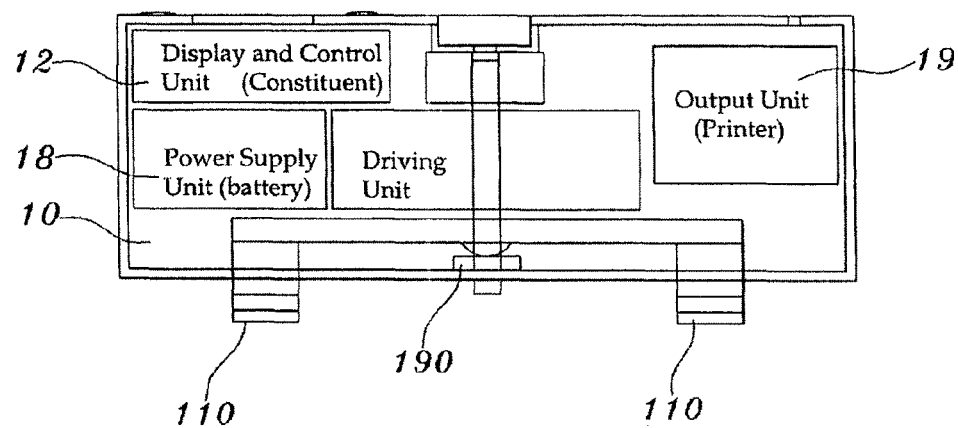
FIG. 18 is a detailed block diagram showing another embodiment of the structure of an upper case in the body of the analysis apparatus according to the present invention.
Figure 19:
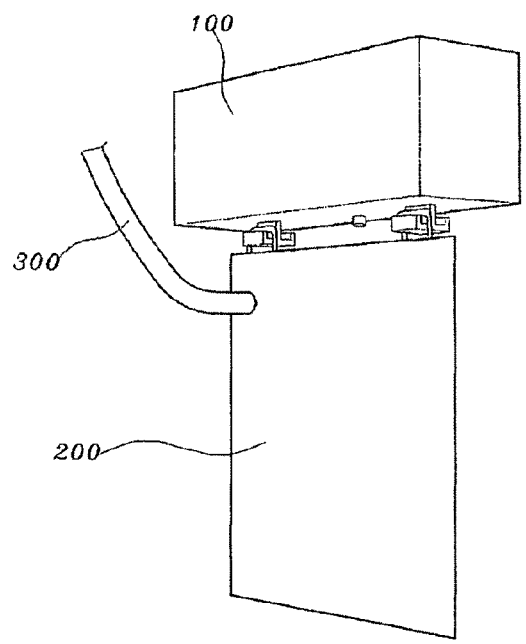
FIG. 19 diagrammatically shows another application example of the analysis apparatus according to the present invention, in which a user reads scales marked on a urine bag connected to the Foley catheter.

As another embodiment of the present invention, an analysis apparatus as shown in FIG. 16 can be useful for a patient with urination troubles such as dysuria. This type of body 100 can be installed at a bedside. For the structure of the body 100, the upper case 10 may be detached/attached from/to the lower case 20 through a juncture 110 having a load cell 190 inserted therein (FIG. 17a); the lower case 20 may slide laterally into and out of the upper case 10 in a lateral direction (FIG. 17b); or the lower case 20 may slide anteroposteriorly into and out of the upper case 10 (in FIG. 17c). These bodies (FIGS. 16-19) have special structural features that the bodies in standard forms shown in FIGS. 1-3 do not have. That is, the load cell 190 coupled to the juncture 110 positioned on the lower end of the upper case 10 enables the body fluid (urine) mass measurement, so that even a patient with urination troubles can measure urine volume and constituents of urine. Differently from the embeddedly mounting method of the load cell 190 shown in FIG. 18, it may be installed on the lower end portion of the lower case 20 (in FIG. 17b).

Returning to FIG. 1, a handle 11 is formed on the upper end of the upper case 10 of the standard-type body 100, and a display and control unit 12 is installed in front of the handle 11. In front of the display and control unit 12 is a joint socket 15 into which an adapter 40 (in FIG. 5) of the body fluid collector is inserted.

These constituents of the standard-type body are equally applied to another embodiment of the analysis apparatus of the present invention shown in FIG. 16 for use with a patient having urination troubles.

An output unit is installed on the lower portion (FIG. 1) or on the rear portion (FIG. 18) of the display and control unit 12. Desirably, the output unit has a built-in printer of small size 19 (in FIG. 3) to thereby output measurement results.

A lid 14 on the top of the upper case 10 covers the cleansing water container.

The lower case 20 is constituted by a container 25 insertedly formed therein, a container handle 21 and a packing 22.

The lower case 20 and the container 25 are disassembled or assembled through a screw 23 on the lower portion.

Reference numeral 32A denotes a body fluid (urine) path formed in the upper body of the adapter. Reference numeral 33A denotes a cleansing water path formed in the upper body of the adapter. Reference numeral 32B denotes a body fluid (urine) path formed in the lower body of the adapter. Reference numeral 33B denotes a cleansing water path formed in the lower body of the adapter.

Here, the body fluid (urine) collector (this has not been explained yet) includes three kinds of constituents: a urine injection nozzle for facilitating suction of a body fluid, a catheter extended to the body, and the adapter positioned at the tip of the catheter, being connected to the body (Further details on these constituents can be referred to Korean Patent No. 44362 to the inventors.).

The catheter of the collector is also formed of three constituents: a catheter for sucking a body fluid (urine or blood) in, a discharge catheter for spraying or jetting cleansing water, and a power line for enabling communication of electric signals between a sensor of the collector and the control unit of the body.

Figure 5:
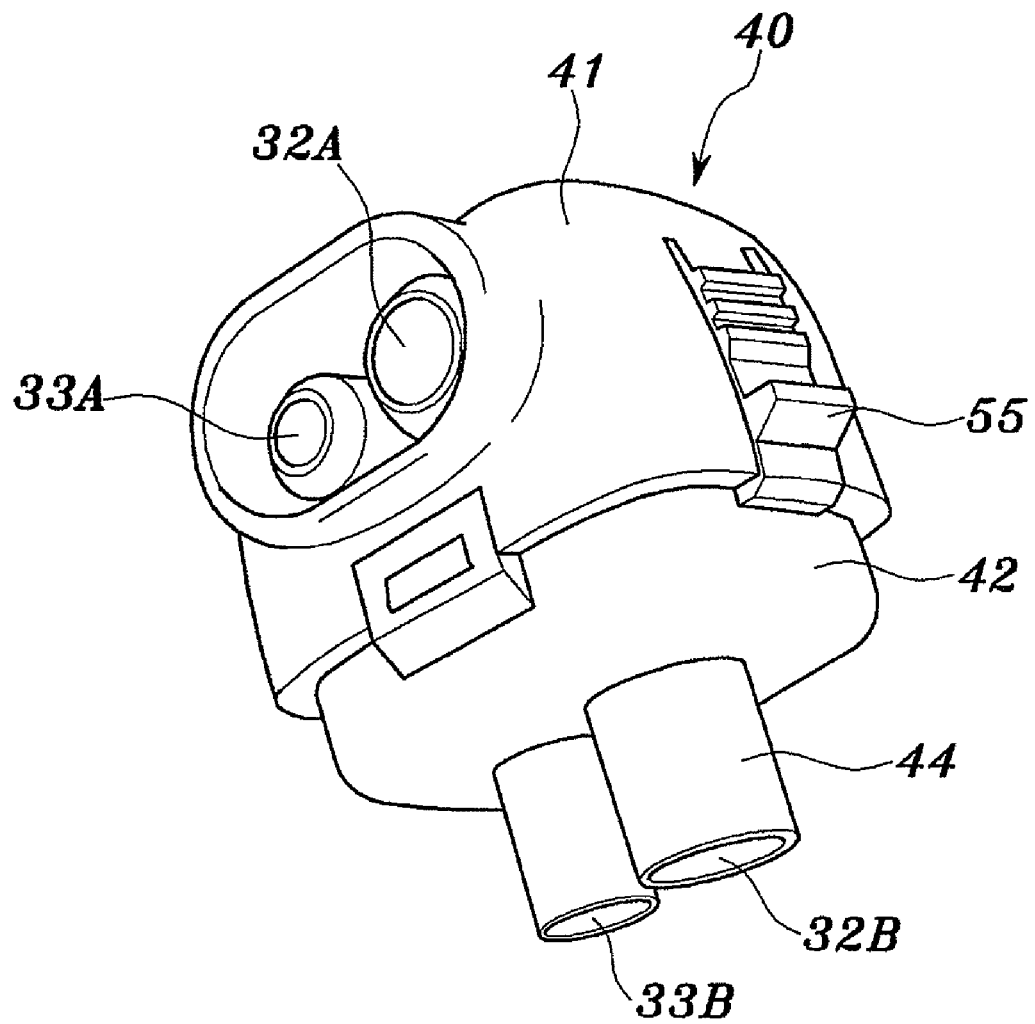
FIG. 5 is a perspective view of an adapter connected to a body fluid collector of the analysis apparatus according to the present invention.

FIG. 5 shows an adapter 40. The adapter is disposed at the tip of the connecting catheter of the body fluid (urine) collector, thereby being connected to the body 100. Now, the adapter will be described.

The adapter 40 (in FIG. 5) plays a role in fixing the body fluid (urine) collector onto the body, and has two important functions as follows.

First of all, it has a built-in sensor 49 for measuring volume of a body fluid (especially, urine volume). Secondly, it has a built-in filter 54 for removing foreign materials or foreign bodies in the body fluid flowing into the body 100.

The lower body 42 of the adapter is made of a transparent material. This is very advantageous from two aspects. First, the adapter needs a transparent structure so that it may be combined with an optical sensor in need of the measurement of urine volume as explained before, and one can easily identify whether foreign materials have been accumulated in the filter inside the adapter.

Two connecting catheters 32A and 33A included in the upper body 41 of the adapter 40 are used as paths that are connected to the catheter 33 of the body fluid collector. Among them, one catheter with a larger inner diameter is the path that a body fluid (urine) 32A flows, and the other catheter is the path that cleansing water 33A for a bidet flows.

As explained before, the adapter 40 consists of the upper body 41 and the lower body 42, and the upper and lower bodies 41 and 42 are fixed onto a suspended step 43 by an elastic fixing piece 48.

Figure 6:
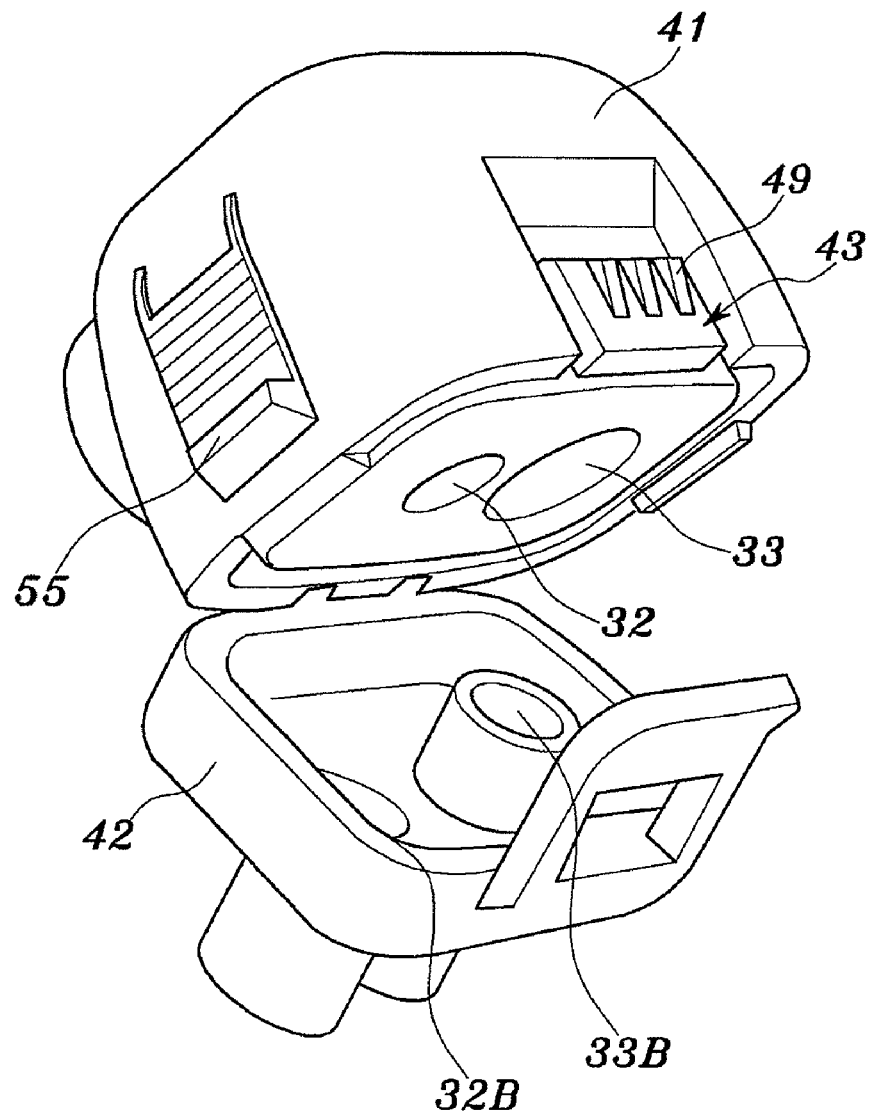
FIG. 6 is a perspective view showing a disassembly of an adapter connected to a body fluid collector of the analysis apparatus according to the present invention.

FIG. 6 shows the elastic fixing piece 48 formed on the lower body 42, and the suspended step 43 formed on the upper body 41 to be in opposite from the fixing piece 48. In this manner, the upper body 41 and the lower body 42 are fitted into each other, creating an easy-to-assemble (dissemble) structure together.

Figure 7:
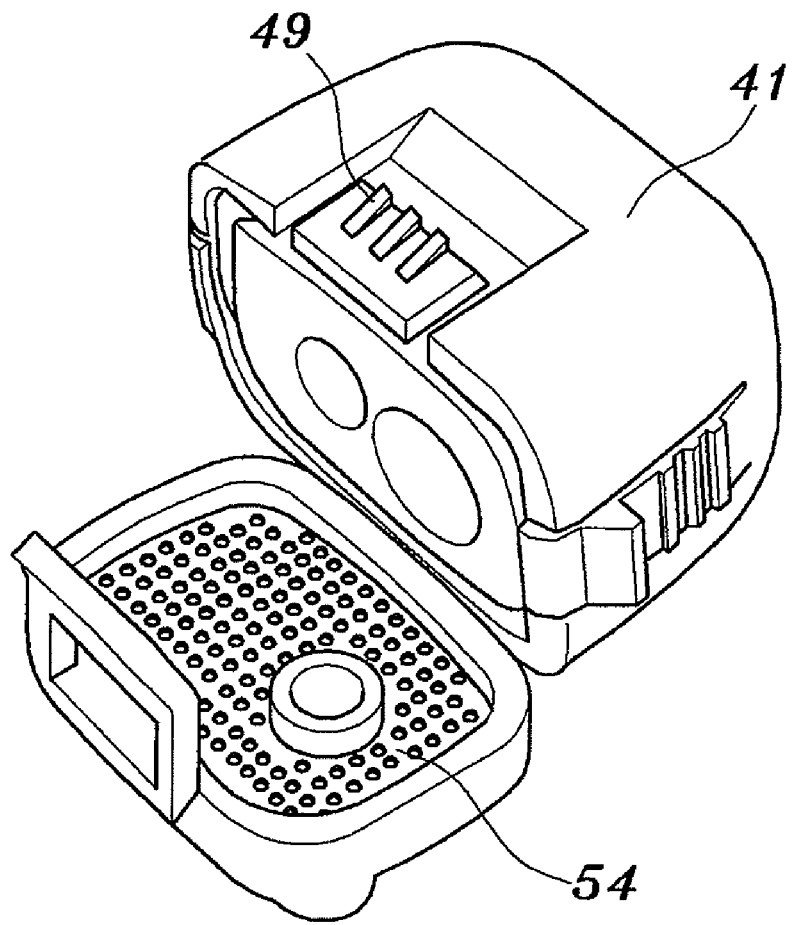
FIG. 7 is a perspective view of a filter inserted into the adapter depicted in FIG. 5.

The adapter is easily dissembled and replaced because the filter 54 is installed inside the lower body of the adapter as depicted in FIG. 7. This filter plays a role in inhibiting foreign materials such as pubic hairs or pieces of tissue from entering the driving unit of the body and further preventing a possible error in the driving unit. Thus, to get rid of those foreign materials stuck in the filter as often as possible, a user should be able to detach the adapter with ease, wash the filter, and reassemble the adapter without difficulty.

Moreover, it is not absolutely necessary to put the filter inside the adapter 40. Thus, the filter may be placed at any position as long as it is in front of the driving unit, and there is no difference in its performance resulted from the position change. It is perfectly acceptable to install the filter in the joint socket of the body, or near the injection nozzle that is used for collecting a body fluid from the collector.

As described above, the upper body 41 of the adapter further includes an electrode 49 (in FIG. 6 and FIG. 7) of a sensor signal transferring unit, in addition to the path 32A of a body fluid (urine) flow and the path 33A of the bidet cleansing water inflow. The electrode can be described as a tip of the body fluid collector of the signal transfer unit. The sensor mounted on the collector sends the control unit a signal informing whether the driving unit should start operating if a liquid gets into the body fluid (urine) collector.

When the adapter 40 is plugged in the joint socket 15 of the body, the electrode 49 (in FIG. 6 and FIG. 7) of the signal transferring unit formed on the upper body of the adapter comes into contact with and bites into the electrode 49B (in FIG. 4) that is formed inside the joint socket 15 to be opposite to the electrode 49. That is, it serves as a transfer channel of an electric signal from the sensor mounted on the collector to the control unit of the body.

Figure 4:
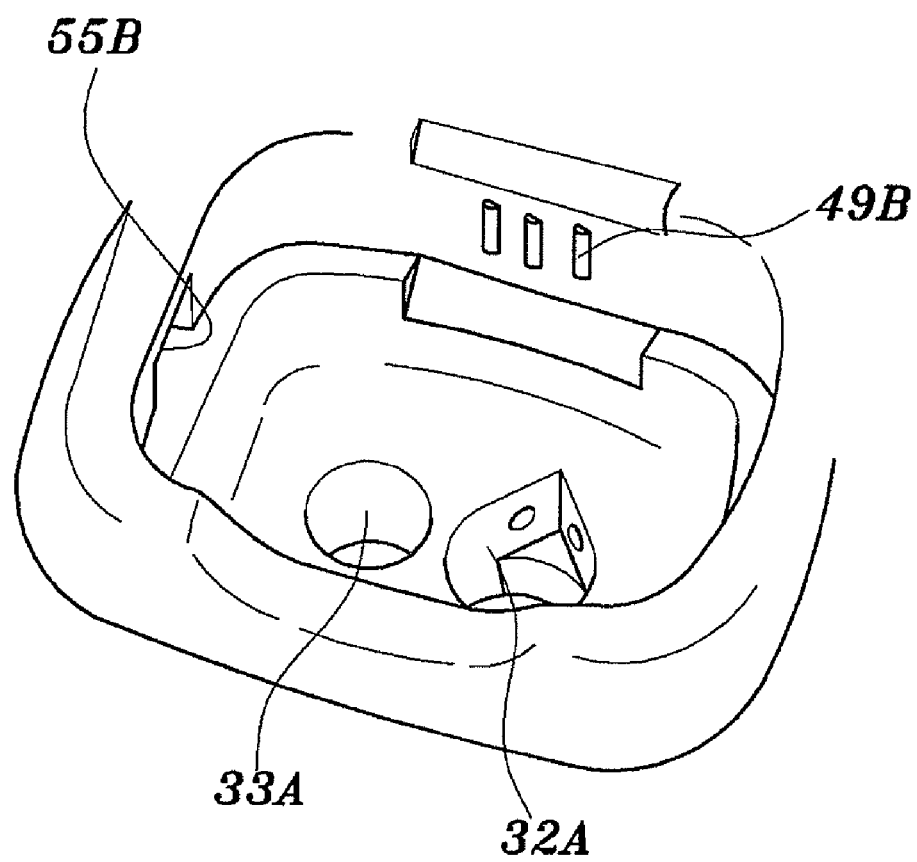
FIG. 4 is a partial perspective view showing a detailed structure of a joint socket of the analysis apparatus according to the present invention.

Referring now to FIG. 5 to FIG. 6, when the adapter 40 is plugged into the joint socket of the body shown in FIG. 4, elastic support pieces 55 positioned on the lateral surfaces on both sides of the upper body of the adapter 40 are forcibly inserted into insertion units 55B in the joint socket to be supported and fixed. This makes it easy to detach/attach the adapter 40 from/to the body 100.

Meanwhile, the body fluid collector is not provided in drawings because the shape of the body fluid collector can be varied, depending on what kind of body fluid out of urea, blood, lymph, urine, saliva, and sweat is collected. Moreover, as explained before, the urine collector disclosed in the previously filed patent application by the inventors may be used as well.

On contrary, the adapter not only has an identical or similar structure independent of the kind of body fluid being used, but also serves as a measuring unit in combination with the body. Therefore, although the adapter is a constituent of the collector, it was dealt in this specification as one of important constituents of the body.

FIG. 3 is a detailed bottom perspective view of the upper case 10 of the body 100 of the analysis apparatus according to the present invention.

The cleansing water container 16 is integrally formed on the one side of the upper case 10, and a discharge unit 35 is integrally formed on the other side of the upper case 10 through the joint socket 15.

The joint socket 15 and the discharge unit 35 are formed in such a manner that they are vertically connected to each other through an internal catheter, and a driving unit M1 (in FIG. 3) is installed between the joint socket 15 and the discharge unit 35. That is, the internal paths 32A and 32B of the adapter passing through in a vertical direction are combined with the joint socket 15 and are connected to the driving unit. Then, they are built in a manner to be able to send a body fluid (urine) to the container 25 in the lower case through the discharge unit 35. Each of these paths is designed as short as possible in a vertical direction (see the blue arrow B in FIG. 10).

Figure 9:
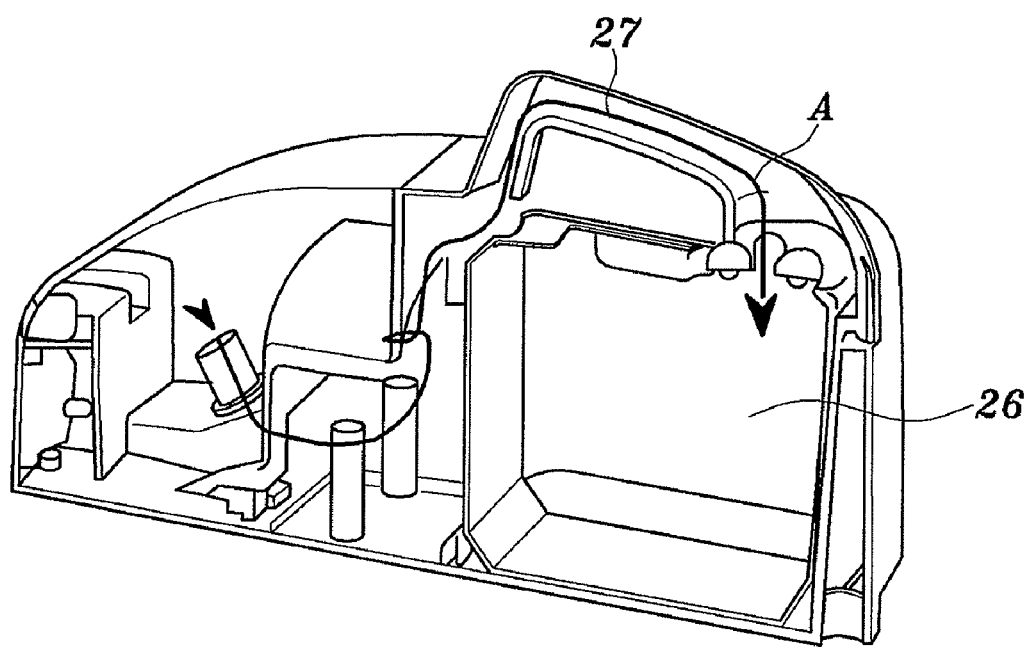
FIG. 9 is a cross-sectional view showing a path of urine flow formed in a urine collecting device disclosed in a previously filed parent application.

This structure shows a great improvement from the disadvantageous structure of the path of the body fluid flow depicted in FIG. 9. According to FIG. 9, the catheter that the body fluid (urine) flows is long and formed in a direction opposite to gravity (see the red arrow A). Thus, the body fluid (urine) remains in the catheter so easily that the problems like corrosion and odor due to the contaminant occur, yet its hygienic management was more difficult.

Figure 10:
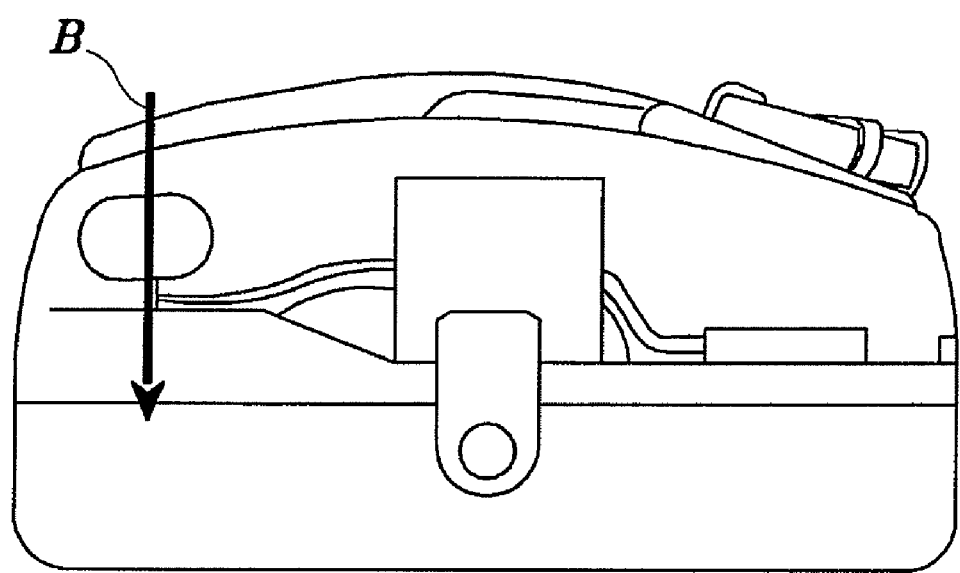
FIG. 10 is a cross-sectional view showing a path of a body fluid (urine) flow formed inside the analysis apparatus according to the present invention.

To overcome such shortcomings, as shown in FIG. 10, the catheter for the body fluid (urine) is now short and formed along the direction of gravity (see the blue arrow B). In this manner, the body fluid (urine) does not remain in the catheter any more, and any one can easily clean and maintain the catheter under hygienic conditions.

Figure 11:
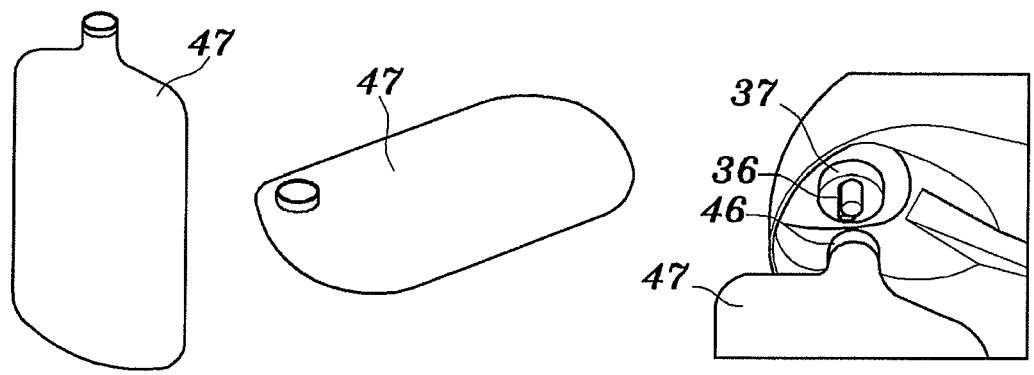
FIG. 11 is a perspective view showing an assembly of a disposable pack used in replacement of a container onto the analysis apparatus according to the present invention.

In replacement of the urine container 25, a disposable pack 47 depicted in FIG. 11 may be used as the container for the present invention. In detail, the disposable pack is mounted in a way that a filter fixture 37 and the disposable pack fixture 46 are rotatably inserted into each other. There is no limitation to the structure, as long as they can easily join with each other.

Figure 8:
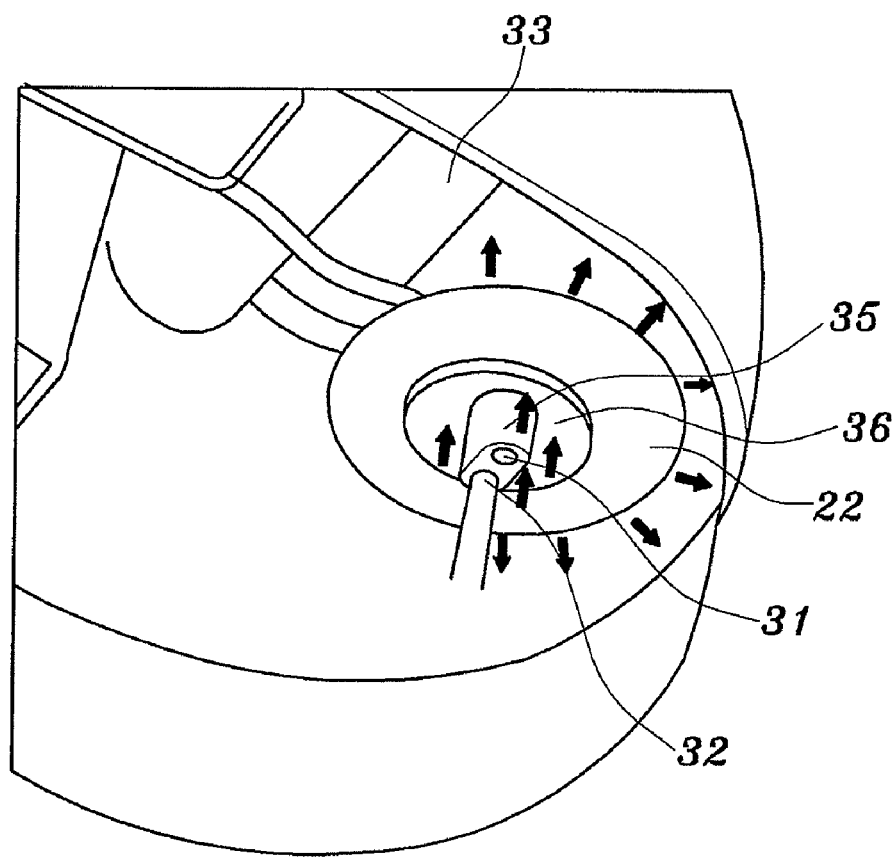
FIG. 8 shows a detailed view of the interior of a packing coupled with a urine container of the analysis apparatus according to the present invention.

FIG. 8 shows a detailed view of the interior of a packing coupled with the urine container of the analysis apparatus according to the present invention.

In FIG. 8, the packing 22 is identical with the packing shown in FIGS. 2a and 2b. The packing 22 is coupled with the container 25 on the lower case 20 to thereby prevent the body fluid (urine) accumulated in the container from leaking outside.

As described before, the interior of the packing 22 includes, sequentially in a vertical direction from the top, the joint socket 15, the driving unit M1, and the discharge unit 35 along the body fluid (urine) paths 32A and 32B inside the adapter, and a donut-shaped filter 36 is fixed around discharge unit 35 at the bottom. When the body fluid (urine) is sucked in and discharged into the container, the odor containing air kept inside the container is pushed outside (see the arrow in FIG. 8). People usually experience a revulsion from this odor. Therefore, the apparatus of the present invention made sure that the odor is first removed through the air purifying filter 36 before it is discharged outside (see the blue arrow in FIG. 8).

The filter can be replaced and washed after a predetermined period of time. Although any kind of air purifying materials may be used for the filter, a material containing activated charcoal powder or zeolite component is desired to maximize the air purification effect.

Reference numeral 19 in FIG. 3 denotes the printer installed on the lower end of the display and control unit 12 shown in FIG. 1. A battery is a charging power supply provided on each side of the rear side of the printer. Here, power supply lines are not shown.

Although the present invention uses a power supply for home use (110-220V) in general, it has built-in charging batteries 18 (in FIG. 3) separately. Therefore, the apparatus may be used even in a place where no power supply is available. This feature shows an improvement from the previous automatic urine collecting apparatus having a bidet system. The prior apparatus uses an external battery and thus, there were a lot of limitations on the moving activities or usage. On the other hand, the present apparatus can be used more conveniently while moving around.

An electrically heating coil is wound around the cleansing water supply line 33 (in FIG. 3). This temporarily increases the temperature of water supplied from the bidet system. This also shows an improvement from the previous bidet system which constantly heated the cleaning water container, even in standby mode. It not only consumed so much power, but also required an additional safety device.

The apparatus of the present invention has the optical sensor 31 (in FIGS. 3 and 4) installed on the lower end of the discharge unit 35. The optical sensor 31 is designed to detect a high water level if the stored body fluid (urine) in the container reaches a certain water level of the discharge unit 35, and sounds an alarm to warn a user to empty the container. This sensor 31 (in FIGS. 3 and 5) for detecting a high level of the container, such as the fluid sensing device disclosed in Korean Utility Model Registration No. 320686 the inventors. Although this is the most preferred configuration, an electrode sensor, a pneumatic sensor, or a simple structure using a float may also be used.

The high water level sensor in the container can equally be applied to the cleansing water container as a cleansing water level sensor (this time, a low water level sensor). The fluid sensing device will be the most appropriate technical means in this case. However, it is perfectly acceptable to use a magnetic sensor having a built-in float as a water level sensor.

To summarize, the analysis apparatus of the present invention has proved major improvements in its structure in the body as follows:

First, the adapter is made of a transparent material so that a user can easily tell from outside when to replace the filter. In addition, as the adapter is easily dissembled and assembled, replacement and washing of the filter can also be done with ease.

Second, the container is isolated and blocked inwardly towards a lower portion away from the other constituents. As such, the other constituents are protected from contamination.

Third, the catheter or the path of the body fluid (urine) flow formed in the apparatus is designed to be as short as possible in a vertical direction. In this way, the body fluid can be drained completely from the catheter, leaving no remainder. Further, the user can clean and maintain the catheter with ease.

Fourth, the disposable pack is used in a detachable manner to maximize user convenience.

Fifth, the air purifying filter is effectively used to remove the odor.

Sixth, the charging batteries built in the apparatus allow the user to get necessary power without difficulty during the moving activity or in usage.

Seventh, power consumption in heating the cleansing water for the bidet is reduced while increasing safety.

Eighth, the sensor can accurately and efficiently check the high water level or the low water level of each container.

By maximizing the convenience in management and hygienic maintenance through the structural improvement of the body of the apparatus, more patients either in hospital or in their homes may rent or lease the apparatus without worrying about the hygienic conditions.

Now, the measuring unit, the control unit, and the output unit of the present invention will be explained in more details.

First of all, the driving unit of the present invention has a suction function of a body fluid and a self-cleansing function through a bidet. These are basic functions identical with those of the driving unit disclosed in Korea Patent Registration No. 494356 to the inventors.

For the suction function, the sensor mounted on the body fluid (urine) collector detects a liquid and sends a signal to the control unit. Then, the controller immediately drives the suction motor M1 (in FIG. 3) to readily suck and store the body fluid (urine) in the container 25.

For the cleansing function of the bidet, cleansing water is sprayed for automatic cleansing under the control of the control unit, after the body fluid (urine) is completely sucked in or if the user wants to use the bidet. In order to perform this function, the cleansing water path 33A used as an internal path of the adapter 40 depicted in FIG. 5 together with the cleansing water supply line 33 (in FIG. 3) forms the inner catheter that is connected to the cleansing water container 16 (in FIG. 3) and processed with a non-oxidizing metallic material (e.g., stainless, titanium and the like). Further, a discharge motor M2 for bidet use is provided between the cleansing water paths 33A and 33B formed in the adapter and the cleansing water supply lines 33 (in FIG. 3).

The measuring unit of different types is now explained.

Quantitative Measuring Sensor

The function of the quantitative measuring sensor is realized by combining the optical sensor placed inside the joint socket 15 of the body and the transparent structure of the adapter 40 included in the body fluid (urine) collector. Detailed structure of each will be described below. The operating principles of each are based on the fluid sensing device disclosed in Korean Utility Model Registration No. 320686 and the flow measuring device using an optical sensor disclosed in Korean Patent Application No 2005-97584.

The lower body 42 of the adapter 40 also consists of a separate body fluid (urine) path 32B and a cleaning water path 33B, and is made of a transparent material.

A prism structure is formed on one side or both sides of the body fluid (urine) path 32B (FIGS. 5 and 6) of the transparent lower body. This transparent prism structure combines with the optical sensor placed inside the joint socket 15 of the body (see FIGS. 12-14 to be described).

In detail, when the adapter 40 is plugged in the joint socket 15, sensor tubes 44, each having a transparent prism structure with the body fluid (urine) path 32B (in FIGS. 5 and 6) of the lower body 42 of the adapter formed thereon, is combined with the optical sensor 31 mounted in the joint socket.

Shortly speaking, the optical sensor 31 having been inserted into the joint socket 15 and combined with the sensor tubes 44 is the one that measures volume of the body fluid (e.g., urine volume) flowing in the body fluid (urine) path.

Figure 12:
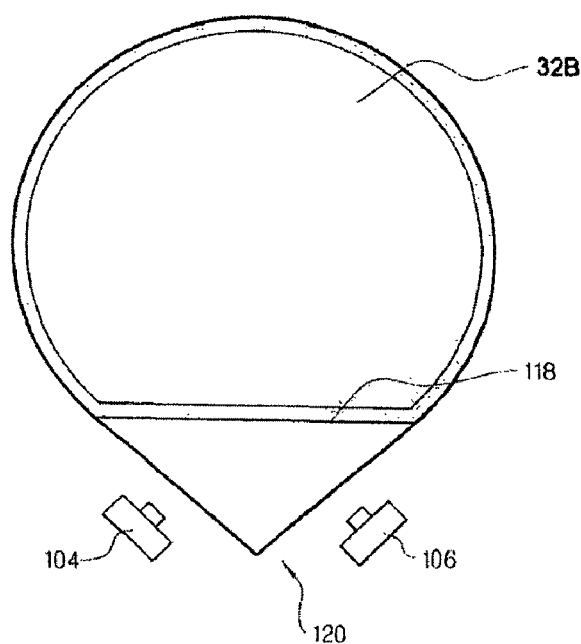
FIG. 12 is a cross-sectional view showing a preferred embodiment of a sensor for sensing the presence of a body fluid (urine) in the analysis apparatus according to the present invention.

Here, the quantitative measuring sensor is built in the adapter 40 at the tip of the body fluid (urine) collector and in the joint socket 15 of the body, respectively. Their operation is not performed until they are combined with each other. FIG. 12 is built based on this optical principle.

A plurality of structures in combination of the prism and the optical sensor may be built, and even more accurate measurement now becomes possible by averaging measurements provided from the sensors.

As such, the measuring means of the present invention is made up of quantitative measuring sensors.

Even though it has been explained that the quantitative measuring sensor is located in front of the driving unit, preferably, in the joint socket 15, it may also be mounted on the discharge unit 35, the body fluid collector, or the urine container.

FIG. 12 is a cross-sectional view showing a preferred embodiment of a sensor for sensing the presence of the body fluid (urine) in the analysis apparatus according to the present invention.

A light-emitting part 104 is installed on the body fluid (urine) path 32B of the lower body 42 of the adapter 40, that is, one outer surface in the joint socket 15 that does not come in contact with the sensor tubes 44 (in FIG. 5), and the front of the light-emitting part 104 faces one side of the prism 120 to thereby radiate light towards the inside of the prism 120. The light towards the inside of the prism 120 reaches a contact surface 118 of the prism 120.

Likewise, a light-receiving part 106 is also installed on the body fluid (urine) path 32B of the lower body of the adapter 40, that is, the other outer surface in the joint socket 15 that does not come in contact with the sensor tubes 44 (in FIG. 5), and the front of the light-receiving part 106 faces the other side of the prism 120 to thereby receive a reflected light from the inside of the prism 120.

Figure 13:
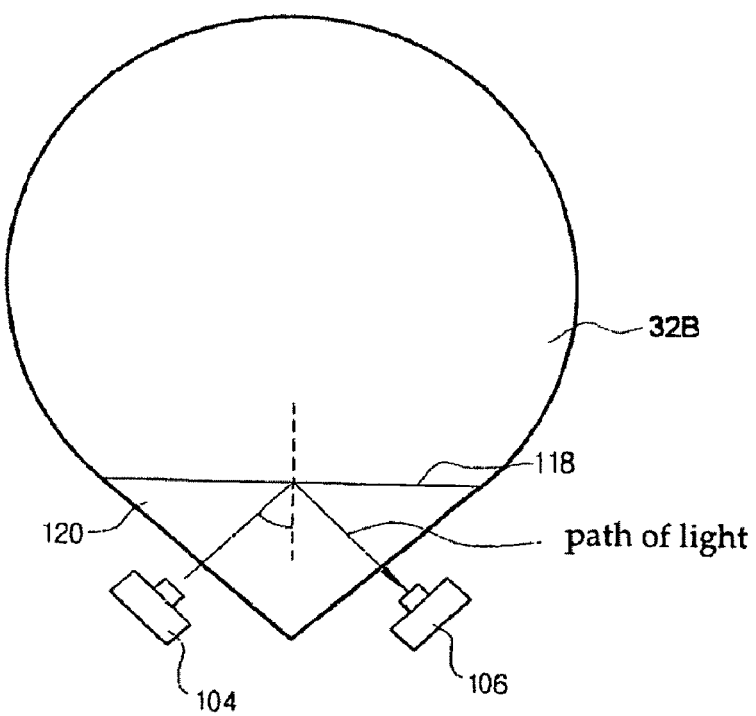
FIG. 13 shows a path of light in a sensor for sensing the presence of a body fluid (urine) in the analysis apparatus according to the present invention, in a case that there is no body fluid (urine)

FIG. 13 shows a path of light in a fluid sensing device including sensor tubes 44 (in FIG. 5), the body fluid (urine) path 32B of the lower body of the adapter in contact with the prism 120, in a case that there is no body fluid (urine) in the fluid sensing device.

As shown in the drawing, light from the light-emitting part 104 to the prism 120 is incident perpendicularly to one side of the prism 120 and then goes straight therein. This light traveling in a straight line inside the prism 120 is incident on the contact surface 118 at an incidence angle (i), and is totally reflected off the contact surface 118. Then, the totally reflected light travels in a straight line until it enters the light-receiving part 106.

Figure 14:
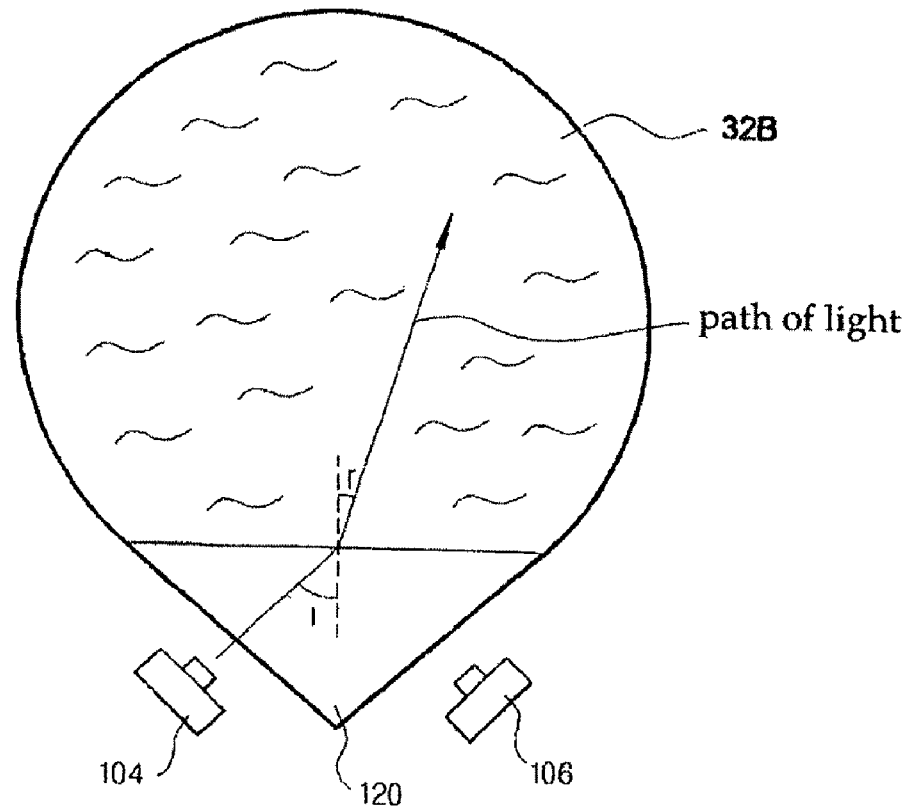
FIG. 14 shows a path of light in a sensor for sensing the presence of a body fluid (urine) in the analysis apparatus according to the present invention, in a case that there is a body fluid (urine)

FIG. 14 shows a path of light in the fluid sensing device including sensor tubes 44 (in FIG. 5), the body fluid (urine) path 32B of the lower body of the adapter in contact with the prism 120, in a case that a body fluid (urine) is in the fluid sensing device.

If the fluid is present, light is not reflected totally. Instead, the light is refracted and enters into the sensor tubes 44 (in FIG. 5), the body fluid (urine) paths containing the fluid.

At this time, for the light to be refracted and incident without being reflected totally, an incidence angle (i) from the prism 120 to the fluid should be smaller than the critical angle.

Going back to FIG. 5, if the first sensor tube 44 contains the fluid, the critical angle θ=sin−1 (N fluid/N prism) (in which N fluid indicates a refractive index of the fluid; and N prism indicates a refractive index of the prism).

Accordingly, for the light to avoid the total reflection and to be incident in presence of the fluid (urine), the incidence angle should be less than the critical angle (the critical angle between the fluid and the prism). Here, the incidence angle varies depending on a material of the prism 120.

Even though it has been explained that one quantitative measuring sensor composed of an optical sensor is used, there may be several of them according to the number of sensor tubes 44 (in FIG. 5). In such case, measurement results obtained from the plural sensors are averaged to improve the accuracy of measurement.

The quantitative measuring sensor composed of the optical sensor includes an ultrasonic generating unit for generating an ultrasonic signal, and an ultrasonic receiving unit in which a sound wave outputted form the ultrasonic generating unit senses the fluid in the catheter. It is also possible to measure volume of the body fluid (urine volume) through an operation using the Doppler Effect.

Some of advantages of using the optical sensor for measurement of the volume of fluid are that because the optical sensor is mounted on the outside of the transparent prism type sensor tube 44, the measuring sensor is not contaminated at all by the body fluid (urine, blood) flowing in the catheters of the body fluid (urine) paths 32A and 32B, so that the measuring sensor can be used permanently, measurement can be done immediately, and hygienic maintenance of the sensor is possible.

These characteristics come to prominence when compared with other kinds of fluid measuring sensors. For example, in case that measurement of the fluid volume is done by reflecting rpm of an impeller inside the catheter, two major problems arise. First one is that the measurement error is great. That is, since both liquid and bubbles contribute to the rotation of the impeller when the fluid (the body fluid, especially urine) flows in the catheter, the measurement error becomes inevitably large. Secondly, the method is unsanitary and electrical troubles occur too often.

Particularly the body fluid (especially urine, blood and so on) contains a large amount of salts and organic substances of diverse kinds, foreign materials are easily accumulated and this interferes with the rotation of the impeller. Needless to say, an excessive accumulation in the foreign materials produces odor and causes contamination. Besides these methods, there is another measurement method using a thermal sensor. Unfortunately however, it cost a lot and the thermal sensor is easily corroded and gets out of order because it is exposed directly to the body fluid.

Qualitative Measuring Sensor for Analyzing Constituents in a Body Fluid

For convenience, the body fluid in the description hereinafter refers to urine as in the measurement of volume of a body fluid. However, it should be noted that constituents in the body fluid are not limited to urine but include specific constituents contained in various kinds of the body fluid (especially, urine and blood).

The body fluid constituent measuring sensor responds to specific constituents in a body fluid (blood, lymph, urine, saliva, sweat and the like), and the same effects are obtained no matter where it is fixed as long as it comes in contact with the body fluid (especially blood and urine).

For instance, a body fluid should be applied a biosensor, the disposable sensor, and the biosensor is inserted into the display and control unit 12 shown in FIG. 1 for analysis of constituents in the body fluid. However, the measurement of specific constituents, data storage in a memory, data output and the like can be carried out, as long as the biosensor is mounted on a portion that comes in contact with the body fluid and has a structure capable of electric signal communications with the control unit. Therefore, similar to the quantitative sensor, the biosensor may be mounted on the injection nozzle in a front portion of the body fluid (urine) collector, the adapter 40 placed at the rear end portion of the body fluid (urine) collector, the front portion of the driving unit of the body, for example, the joint socket 15 into which the adapter of the collector is plugged or the rear portion of the driving unit, the discharge unit 35, or the container.

The body fluid constituent measuring sensor is composed of a biosensor BS containing enzymes.

Desirably, the biosensor disclosed in the previously filed Korean Patent Application No. 2005-51645 is used.

This biosensor has a self-assembly single layer for film immobilization. A fixed film of the single layer is prepared with 3-mercaptopropionic acid.

In case of the aforementioned biosensor, porous silicon is used as a substrate because the sensitivity thereof is about three times higher than a planar electrode so that specific constituents in the body fluid can be measured more effectively.

Within the scope of achieving the objectives of the present invention, other kinds of sensors, such as a properly manufactured immunity sensor, a DNA sensor, a cell sensor, a laboratory chip and the like, may also be used, in place of the enzyme sensor.

The following now describes the control unit.

In addition to the control of operations of the driving unit and sensors in each container conducted by the control unit disclosed in Korean Patent Registration No. 494365, herein incorporated by reference, the display and control unit 12 of the present invention has two additional functions, namely, the control of operations of the measuring unit and the output unit.

Moreover, under the control of the control unit, the memory unit stores measurements of volume of the body fluid and data values of specific constituents obtained by the measuring unit; and the data values are substituted to given equations (Equations for ★ FE $Na^+$ value and Renal Failure Index value provided in Table 2) for operation. Based on the operation result, the control unit is able to diagnose and evaluate the conditions of a patient.

For example, when an operation result obtained by substituting $Na^+$ concentration in the urine, Cr concentration in the urine, $Na^+$ concentration in the blood and Cr concentration in the blood to the Equation given in Table 2, ★ FE $Na^+$=Urine ($Na^+$/Cr)/Plasma ($Na^+$/Cr), is greater than 1, the control unit makes a diagnosis that a patient has a problem in his kidney. On the other hand, if the operation result is less than 1, the control unit makes a diagnosis that a patient has a problem in his circulatory system.

Likewise, an operation result of the Equation ★ Renal Failure Index=U ($Na^+$)/GFR=Urine $Na^+$/(Urine Cr/Plasma Cr) may be utilized for a diagnosis.

Next, the output unit is explained.

The output unit of the present invention serves as a means for outputting measurement values obtained by the measuring unit, and includes a display unit and a printer 12 (in FIG. 1) for outputting a measurement value.

The output unit includes a built-in printer, an LCD, a USB port, a wired/wireless output device, etc. Among them the printer may be installed externally to the apparatus.

The USB port enables to transfer and store data through an external memory element. The output unit may further include an RF device or a Bluetooth chip for wireless communication. Through these configurations, one can transfer all data obtained from a body fluid of individual patient in a sickroom (or patient room) benefiting from the analysis apparatus of the present invention to the main computer of a ward in a real time mode, whereby indicating a possibility of more efficient health care management.

Figure 15:
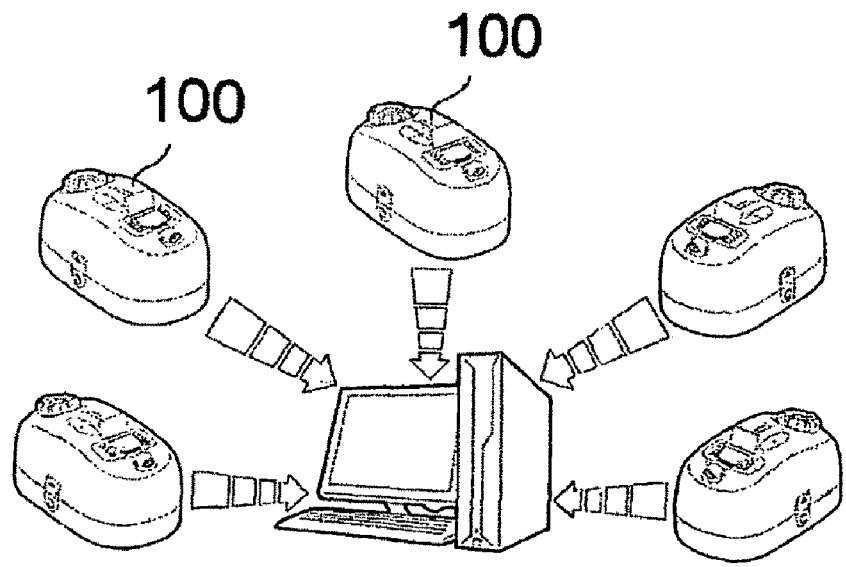
FIG. 15 is a perspective view for diagrammatically showing an example of data communication between the analysis apparatus of the present invention and a computer.

Besides, since the connection with a personal computer through a USB port can be connected to the main computer of a hospital over Internet as shown in FIG. 15, an attending physician can be provided with data of the body fluid of a patient in his home directly from the patient. This also opens up the possibility of establishing a basis for telemedicine.

Further, the present invention utilizes the load cell in order to measure the urine volume based on the mass measurement principle. The load cell may be mounted in a detachable manner onto a front surface or a lateral surface of the apparatus. In particular, the load cell is advantageously used for patient having urination troubles.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The present invention is capable of detecting a body fluid (urine) in the body fluid (urine) collector with a sensor, the body fluid being drained from a patient suffering from deficiency in the circulating blood in result of medial or surgical emergency; automatically sucking the body fluid, accurately measuring urination time and urine volume; storing or recording the measurement in a memory; outputting the recorded data; performing, in the control unit, an operation of Equations FE $Na^+$ value and Renal Failure Index value given in Table 2; and enabling the medical staff to make a quick diagnosis in field based on the operation result, whereby the medical staff can take all necessary measures without delay for improving the patient's condition.

In addition, patients without urination troubles do not need to use the insertion type Foley catheter any longer. Accordingly, a urinary system infection that is the typical side effect of the existing catheter can be substantially reduced. Considering a fact that antibiotic resistant strains in a hospital are being increased greatly partially in result of the secondary infection in the urinary system caused by the catheter, patients having severe underlying disease or poor immunity can be susceptible to the urinary system infection, further to the hematogenous infection, eventually causing a loss of life. To the patients in these conditions, the apparatus of the present invention actually plays a very important role.

Traditionally, it used to take more than 24 hours to get the result of a qualitative analysis on a body fluid (urine and blood) in need of the renal function test after a body fluid sample had been sent to a clinical laboratory. On contrary, the apparatus of the present invention is provided to any patient who needs it, and the patient can personally measure the volume of his body fluid (urine and blood) and the constituents in the body fluid within about one minute. Thus, medical staff is able to take all necessary measures immediately, so as to improve a patient's condition.

Nowadays, angiography is frequently performed in treatment of all kinds of vascular diseases (e.g., cerebral infarction, myocardial infarction, etc.), and a contrast medium is typically used in this procedure. However, it is reported that the contrast medium can cause a severe renal scar as part of its side effect, current medical staff cannot find out its result until 24 hours later. In field, a variety of drugs having renal toxicity are actually used for treatment. Although these drugs rapidly destroy renal cells and progress an acute renal disease, there has not been a means until now to help medical staff detect the condition of such patient soon enough. Many practitioners depend on their clinical experiences, and sometimes they cannot do much either even if a renal scar is caused because of a delayed treatment (after 24 hours). Especially, once a renal cell is scarred, it does not do cell division ever. Therefore, the importance and superiority of the present invention become even greater in consideration of the fact that the scarred renal function cannot be recovered forever.

That is, according to the present invention, besides the evaluation of acute renal diseases, early diagnosis and prognosis of a chronic renal disease are now possible. In detail, after measuring particular indexes such as glucose, protein, blood urea, blood Cr, pH of urea and son on, one can approach a more accurate treatment for a chronic renal failure and further expect a prognosis thereof. Above all, the present invention can greatly contribute to the improved health care of a diabetic renal disease.

Moreover, besides the major clinical effects described above, the present invention promoted the efficiency of human resource management associated with the medical staff. In the past, a medical staff should personally check and record a patient's urine volume accumulated in a urine bag every hour. However, the present invention is capable of automatically keeping the records of a patient's urination time, urine volume each time, total urine volume per day, average urine volume each time, and conditions of urine. Therefore, whenever medical staffs need such data, they can get desired data any time without delay.

According to the effects of the present invention, it is now possible to make a diagnosis, prognosis and evaluation management with diverse urination related diseases including urinary incontinence, prostate hypertrophy, urinary frequency, enuresis, diabetes insipidus and the like. Also, patients with chronic vaginal diseases in their homes can transfer measurements on the constituents in their body fluids and urine volumes to their attending physicians on the regular basis through the USB port in connection with a personal computer of each patient. As telemedicine becomes possible, a greater number of patients in their homes can be taken care of by a hospital at the same time and at high efficiency. As medical services are available in home, the convenience of a patient is also maximized.

Differently from the standard type structure, the present invention introduced the detachable body structure in a box-shaped case using a urine bag connected to the conventional catheter or an insertedly mounted load cell especially for patients with urination troubles. This structure enables the mass measurement—based analysis on urine volume and constituents of urine in a real time mode, so all patients, regardless of urination troubles, can be provided with the quantitative and qualitative analysis on their body fluids. With these exceeding advantages and effects, the present invention is indeed a very useful invention in health and medical service industry.

The invention claimed is:

1. An analysis apparatus for bodily fluids, comprising:
a bodily fluid container, the bodily fluid container comprising:
an upper case having a top wall;
a joint socket formed in the upper case top wall;
a lower case detachably joined to the upper case, the lower case having a top wall;
an opening formed in the lower case top wall, the opening being vertically aligned with the joint socket to form a fluid flow path;
a discharge unit on the upper case mating with the opening in the lower case top wall; and
a transparent adapter in the joint socket, the adapter defining a first path for bodily fluids and having a connector for joining with a bodily fluid collector;
a cleansing water container for storing cleansing water used for cleansing;
a driving unit for moving the body fluid from the bodily fluid collector into the bodily fluid container and for moving the cleansing water in the cleansing water container into the bodily fluid collector;
a control unit for controlling operation of the driving unit;
a measuring unit for measuring quantitation and constituents of bodily fluids flowing through the fluid flow path, the measuring unit comprising an optical sensor in the joint socket for measuring fluid flow through the adapter;
an output unit for outputting a measurement value obtained by the measuring unit, the measuring unit and the output unit being housed in the apparatus;
a cleansing water path in the adapter; and
a cleansing water supply line extending between the cleansing water container and the adapter.

2. The apparatus of claim 1, wherein:
the cleansing water container is in the upper case.

3. The apparatus of claim 1, further comprising:
a filter in the adapter.

4. The apparatus of claim 3, wherein the filter is replaceable.

5. The apparatus of claim 3,
wherein the filter is visible while in the adapter.

6. The apparatus of claim 1, further comprising:
a display unit for displaying the results of the first sensor.

7. The apparatus of claim 1, further comprising a packing around the opening in the lower case, the packing including an air filter.

8. The apparatus of claim 1, further comprising:
a control unit for receiving signals from the optical sensor; and
an output unit for providing results to a user.

* * * * *